United States Patent [19]

Gavriely

[11] Patent Number: 4,848,324
[45] Date of Patent: Jul. 18, 1989

[54] TREATMENT METHOD FOR SHOCK

[75] Inventor: Noam Gavriely, Haifa, Israel

[73] Assignee: Technion Research & Development Foundation Ltd., Haifa, Israel

[21] Appl. No.: 119,377

[22] Filed: Nov. 12, 1987

[30] Foreign Application Priority Data

Nov. 12, 1986 [IL] Israel ........................................ 80598

[51] Int. Cl.⁴ ........................ A61F 13/08; A61H 11/00
[52] U.S. Cl. ................................. 128/24 R; 128/165; 128/327
[58] Field of Search ............... 128/155, 156, 157, 160, 128/158, 165, 166, 325, 326, 327, 24 R, 1 D, 24.3; 2/242; 36/2 R

[56] References Cited

U.S. PATENT DOCUMENTS

| | | | |
|---|---|---|---|
| 800,467 | 9/1905 | Myers | 128/327 X |
| 2,574,873 | 11/1951 | Jobst | 128/165 |
| 2,582,648 | 1/1952 | Mowbray | 128/165 X |
| 3,856,008 | 12/1974 | Fowler et al. | 128/165 |
| 3,933,150 | 1/1976 | Kaplan et al. | 128/24 R |
| 3,968,792 | 7/1976 | Small | 128/165 X |
| 4,084,586 | 4/1978 | Hettick | 128/165 X |
| 4,180,869 | 1/1980 | Pedergrass et al. | 128/165 X |
| 4,228,792 | 10/1980 | Rhys-Davies | 128/327 X |
| 4,355,632 | 10/1982 | Sandman | 128/24 R |
| 4,577,622 | 3/1986 | Jennings | 128/24 R |

*Primary Examiner*—Richard J. Apley
*Assistant Examiner*—David J. Bender
*Attorney, Agent, or Firm*—Browdy and Neimark

[57] ABSTRACT

The invention relates to a method and device for an emergent treatment of hypovolemic shock caused by loss of blood. According to the new method an elastic covering tube is applied onto the injured part of a patient's body, said tube possessing two main characteristics: (1) it is twisted along its horizontal axis as a rolled-up tube the end of which is rolled onto said body parts and (2) the material used for the elastic tube has to provide a pressure of between 100 to 400 mm Hg and to possess a critical elasticity coefficient. The critical elasticity coefficient being defined by a given formula which correlates the thickness of the material, unstretched radius and length of the tube, and length and radius of the injured part of the body to be covered.

3 Claims, 1 Drawing Sheet

TREATMENT METHOD FOR SHOCK

The present invention relates to a new method for shock treatment. More particularly, the invention relates to a new method for an emergent treatment of shock caused primarily by loss of blood through internal bleeding, or injury of the human body or as encountered under the name of hypovolemic shock, but also in other types of shock caused by sepsis or anophilosis.

BACKGROUND OF THE INVENTION

The term shock, used already in the 19th century, was defined to characterize the alarming symptoms known to result from a wide variety of causes, both physical and psychic. One of the most frequently encountered types of shock is the traumatic one, caused after severe injury. As a result, a disturbance of fluid balance occurs which is manifested by a decreased volume of blood and tissue perfusion. Other changes, both chemical and pathologic may occur in a traumatic shock, including decreased coagulability of the blood.

There is a substantial agreement among all authorities in respect to the fact that incompatibility between blood volume and vascular volume due to loss of blood or other body fluids by whatever means or by pathologic dilatation of the vascular bed, is considered the most important initiating factor in shock. Accordingly there is a search for devices which provide an easy and immediate treatment for shock. In this connection it is perhaps interesting to cite a publication on this subject by Dr. R. L. Krome (Annals of Emergency Medecine, Aug. 14, 1985, 14/713): "It is fascinating that shock, considered at one time to have been researched out, is now fully resuscitated as a field of study". Early investigations examined a wide variety of possible therapeutic routes without fully understanding the pathophysiology of the problem. Today it is generally understood that although shock is associated with and is usually diagnosed mainly by a systolic blood pressure reading of less than 80 to 90 mm Hg, it is the reduced perfusion of few critical organs (namely the heart, brain, kidneys, liver and the intestines) which cause the severe pathophysiological consequences of shock. Among the events which cause shock the following are particularly mentioned: spontaneous rupture of blood vessels, i.e. abdominal aneurism, leg veins esophageal vasices etc., any accident which causes severe blood loss through an open injury, and sepsis or anaphylaxis which cause pathologic dilatation. Treatment of shock depends to some extent on the nature of the injury or disease responsible for its develoment. Attention is first directed to restoration of adequate balance between blood volume and vascular volume and to prevention of further loss of blood. In case of severe injury to the extremities, the part is immobilized. Prevention of loss of body heat is accomplished by use of covers; also elevation of the legs may be helpful to enable the draining of blood from the legs back into the critical organs such as the heart, brain kidneys and lung circulation so that they are re-supplied with oxygenated blood. The usefulness of simple bandage applied the legs is limited in returning blood to the central vessels due to the range of pressure required.

After the second world war, an elegant device for shock treatment was suggested. It is the so called Medical Anti-Shock Trousers (MAST). The device is designed to counteract hypovolemic shock by the application of counterpressure around the legs and abdomen, producing an artificial peripheral resistance, and ensuring adequate to the critical organs perfusion. The device has the configuration of trousers, wherein air chambers surrounding the legs and abdomen can be inflated and deflated individually by the aid of air compression. The basic principle in the MAST application is to create an artificial peripheral resistance and decrease in transmural pressure. Thus, bleeding is arrested, external vascular space is minimized and organ perfusion is sustained. However, the application of MAST has some undesirable effects such as decreased pulmonary vital capacity. Also abdominal discomfort is encountered in some patients. The main disadvantage is the fact that the pressure in MAST is uniformly applied on all the parts of the human organs, which will of course delay the return of the blood into the recirculation stream and possible trapping of the blood distal to the pressure point.

Another disadvantage of the MAST device is encountered and some delay results thereto regarding the further treatment of the injured person, when the MAST device has to be removed. Moreover, consideration should be given to the fact that this device is quite expensive and not for "one-time" use.

SUMMARY OF THE INVENTION

It is an object of the present invention to provide a simple method for the treatment of hypovolemic shock with a simple and inexpensive device which can be used by unskilled persons. Thus, the invention consists of a method for an emergent treatment of hypovolemic shock by applying onto the portion of the patient's body an elastic protective tube resembling a sock, said covering tube being characterized by the following:

(a) it is twisted along its horizontal axis as a rolled-up tube the end of which being rolled onto the injured part;

(b) the elastic constant (K) of the material used in order to provide a pressure (P) of between 100 to 400 mm Hg. is presented by the following formula:

$$K = \frac{2P \cdot h^{\frac{1}{2}}}{\pi^{3/2} (1 - r_o/r)(L_o - L_1)^{\frac{1}{2}}} \text{ wherein}$$

h = thickness of the material;
$r_o$ = unstretched radius of the tube;
r = radius of the portion of the body to be covered;
$L_1$ = length of the portion of the body to be covered; and
$L_o$ = length of the tube.

As appears from the above formula, the elasticity of the material is very important in order to provide the adequate treatment for the shock state. By applying the covering tube onto the injured part from its distal end to the proximal one, the blood is forced from the more peripheral blood vessels to the central one and to the heart. A portion of the rolled up tube remains rolled up so as to provide radial tension around the proximal portion of the organ, thus impeding the flow of blood to the periphery of the body and providing increased peripheral resistance and more circulating blood to the critical organs (i.e. heart, brain, kidneys etc.). In addition using this method, the useful result of preventing blood loss from open injuries to the parts covered by the device is obtained.

In contrast to the MAST device which requires a trained team for applying it to the injured body, according to the present invention the device can be easily applied even by unskilled person. Whereas the device is very simple and inexpensive, it is disposable after one-time use. Also the further treatment of the injured person can be immediately carried out at the hospital, by simply cutting the elastic protective covering tube.

The material from which the elastic protective tube is made, is selected from various compounds such as natural rubber (so called latex), synthetic rubbers such as neoprene and polybutadiene. These compounds possess the adequate elasticity which conforms the above equation. Of course slight deviation of ±20% in the elastic constant are admissible, this depending on the specific organ to be covered as well as to the extent of pressure required in order to push the blood into the circulation stream.

In contrast to the MAST device, which was found to cause a decrease in the pulmonary vital capacity, the device according to the present invention does not impart this deficiency. This seems to result from the gradual pressure applied onto the injured organ produced upon the movement thereof of the rolled tube. This is also a very important advantage, since as known, a decrease in the pulmonary vital capacity may be a critical factor in patients with respiratory insufficiency.

The method and device according to the present invention are particularly useful in the initial treatment of shock in the field when patients in shock require transportation to a hospital and when patients are in a severe state of shock in the emergency room.

SHORT DESCRIPTION OF THE DRAWINGS

FIG. 1 is a side view of the elastic protective tube, with its upper end rolled-up, as applied onto an injured leg; and FIG. 2 is a side view of the device before its application with the elastic protective tube almost completely rolled up.

DESCRIPTION OF A PREFERRED EMBODIMENT OF THE INVENTION

Figures 1, 2:
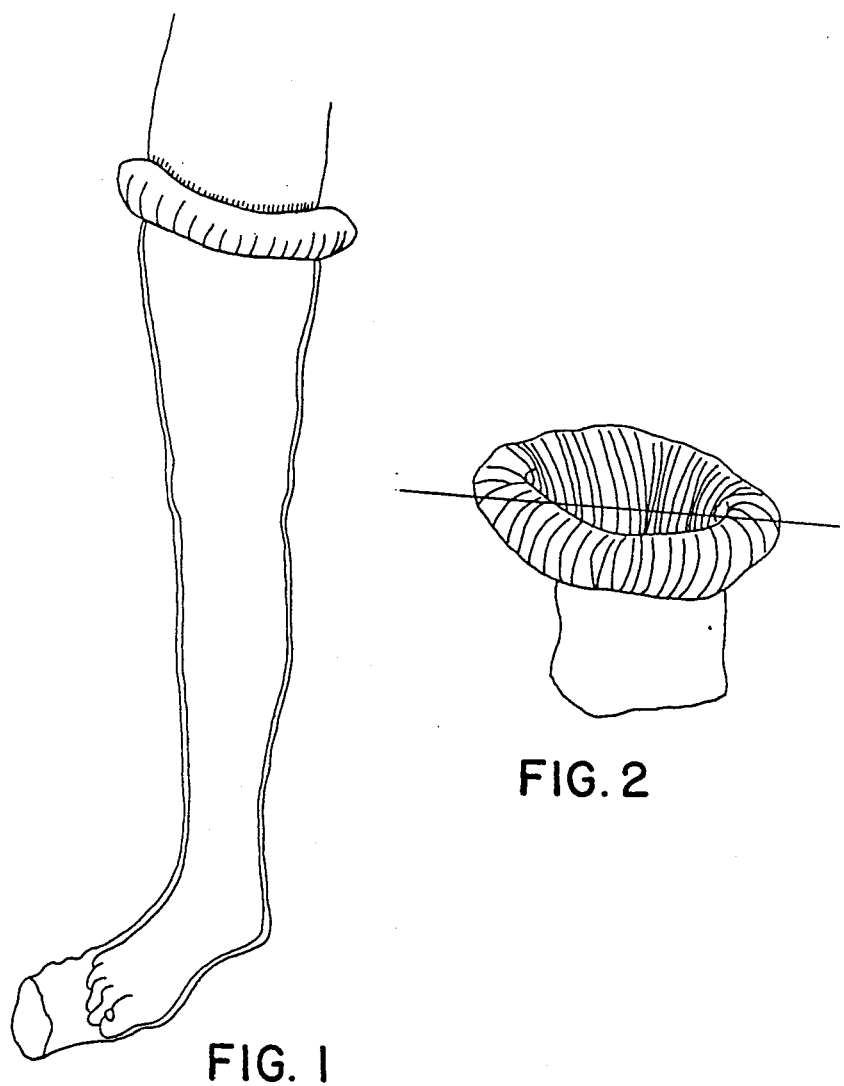

As appears from FIG. 1, the rolled up end of the elastic protective tube is applied onto the injured part (i.e. a leg in the Figure). When the tube is unfolded to the desired level onto the leg, by moving the rolled-up end, it gradually applies certain pressure to the respective tissue which effectively squeezes the blood from the underlying blood vessels. The pressure created by the tension in the rolled-up protective tube, is greater than the arterial blood pressure of the patient. This procedure is then repeated with additional rolled-up covering elastic tubes, in other extremities of the body or even over the entire lower part of the body according to the particular requirements. Here again, there is a clear advantage over the MAST unit whereby the device is covering the entire body thus applying thereto a corresponding pressure although this might not be required and sometimes even being harmful.

According to another embodiment, it is possible after the device was applied, to make some holes or even cut a surface in the protective tube, without affecting the pressure applied onto the proximal portion of the injured limb. This might be desirable when it is needed to exposure any portion of the limb distal to the circular band which impedes the flow of the blood to the injured limb.

It is also possible to use the device in orthophedical surgery, in which case the material used should be sterilized.

In conclusion, the device according to the present invention is very simple and can be easily applied without substantially causing pains to the patients. Thus is in contrast to the MAST suits, which are considered by all skilled in the art to be painful and not always recommended to be used. The device is also very versatile in its application; as appear from the formula given above which combine a number of parameters such as thickness of material, radius of the tube, radius of the part, length of tube, length of the part and elasticity of the material, it is possible to select the proper parameters according to the particular case to be dealt with.

What is claimed is:

1. A method for emergent treatment of hypovolemic shock, comprising the step of:
   applying a gradual pressure to a portion of a patient's body without any decrease in the pulmonary vital capacity, by inserting a distal end of said portion of said patient's body through a sock-shaped covering tube having a free end and a stationary end, said tube being applied as a roll with said free end of said tube being radially outward of said stationary end; and then,
   unrolling said tube so that said stationary end remains stationary along said portion of said patient's body while said free end moves proximally along said portion of said patient's body until all of said portion of said patient's body is covered, thus providing a radial tension around said portion of said patient's body whereby said covered portion of said patient's body is exsanguinated.

2. A method according to claim 1, wherein a portion of the rolled tube remains rolled in order to provide radial tension around a proximal portion of the extremity.

3. The method of claim 1, wherein said tube has an elastic constant (K) and provides a pressure (P) on said portion of the body of between 100–400 mm Hg according to the following equation:

$$K = \frac{2Ph^{\frac{1}{2}}}{\pi^{3/2} [1 - r_o/r] [L_o - L_1]^{\frac{1}{2}}}$$

wherein:
   h = thickness of the material,
   $r_o$ = unstretched radius of the tube,
   r = radius of the portion of the body to be covered,
   $L_1$ = length of the portion of the body to be covered,
   $L_o$ = length of the tube; and P is between 100 to 400 mm Hg.

* * * * *